United States Patent [19]

Shinohara

[11] Patent Number: 4,567,366

[45] Date of Patent: Jan. 28, 1986

[54] METHOD AND APPARATUS FOR MEASURING METHANE CONCENTRATION IN GAS

[75] Inventor: Akio Shinohara, Fujisawa, Japan

[73] Assignee: Showa Denko Kabushiki Kaisha, Tokyo, Japan

[21] Appl. No.: 536,051

[22] Filed: Sep. 26, 1983

[30] Foreign Application Priority Data

Sep. 25, 1982 [JP] Japan .................. 57-166836
May 18, 1983 [JP] Japan .................. 58-86770
Jul. 28, 1983 [JP] Japan .................. 58-136727

[51] Int. Cl.$^4$ ............................................. G01J 5/08
[52] U.S. Cl. .................................... 250/339; 250/343
[58] Field of Search ............... 250/339, 343, 341, 340, 250/338 GA, 344, 345; 356/437

[56] References Cited

U.S. PATENT DOCUMENTS 4,266,878 5/1981 Auer .................................... 356/419

FOREIGN PATENT DOCUMENTS 2534 1/1981 Japan .................................. 250/339
2535 1/1981 Japan .................................. 250/339

OTHER PUBLICATIONS

H. Inaba, T. Kobayasi, M. Hirama and M. Hamza, "Optical-Fibre Network System for Air-Pollution Monitoring Over a Wide Area by Optical Absorption Method", Electronics Lett., 15 (1979) pp. 242-244.

Primary Examiner—Alfred E. Smith
Assistant Examiner—Constantine Hannaher
Attorney, Agent, or Firm—Sughrue, Mion, Zinn, Macpeak and Seas

[57] ABSTRACT

A method and apparatus for measuring the methane concentration in a gas, which comprises transmitting light having at least one wavelength band selected from a band of 1.6 μm and a band of 1.3 μm through an optical fiber having a small transmission loss in said wavelength bands to a measuring cell where an ambient gas comes in and out, absorbing the light in at least one characteristic absorption wavelength of methane gas, selected from a wavelength of 1.666 μm and a wavelength of 1.331 μm, in said measuring cell, transmitting the light through an optical fiber having a small transmission loss in at least one wavelength band selected from a band of 1.6 μm and a band of 1.3 μm to a bandpass filter, separating the light into at least one light having the methane gas absorption wavelength, that is, the wavelength to be measured, and at least one light having other reference wavelength, determining the intensity ratio of the light having the wavelength to be measured to the light having the reference wavelength, and calculating the methane gas concentration in the measuring cell from the so-determined intensity ratio.

14 Claims, 11 Drawing Figures

METHOD AND APPARATUS FOR MEASURING METHANE CONCENTRATION IN GAS

BACKGROUND OF THE INVENTION

1. Field of the Invention

The present invention relates to a method and apparatus for measuring the methane concentration in a gas, which are particularly useful for measuring the methane concentration in a liquified natural gas (LNG) tanker, an LNG tank or a pit of a coal mine at a distant point.

2. Description of the Prior Art

Methane gas is very important as a fuel gas and is contained in a large quantity in natural gas. With recent increase of the calorific value of the city gas, natural gas has been taking the place of coal gas. Accordingly, in order to prevent occurrence of a gas explosion due to leakage of the city gas, it is eagerly desired to develop a safety system for detecting leakage of a methane gas promptly and assuredly in an underground market, a multi-storied building or the like and giving an alarm.

Methane gas is a main component of a coal mine gas produced in a coal mine, and development of a similar system is desired for preventing an explosion of the coal mine gas and a subsequent explosion of coal dust.

Conventional methane gas sensors of the contact burning type, heat conduction type and semiconductor type are insufficient in the gas selectivity and response characteristics because of the measurement principles of these sensors, and the reliability is readily influenced by the co-present gas, temperature and humidity. Accordingly, these conventional methane gas sensors are not suitable for the measurement in a stope where the measuring conditions are strict, and the real time measurement is difficult. Furthermore, in case of remote inspection and remote measurement, since electric signals are transmitted, a risk of occurrence of an error due to electromagnetic induction or an accident due to damage of a cable cannot be neglected.

SUMMARY OF THE INVENTION

It is the primary object of the present invention to provide a method and apparatus for measuring the methane concentration in a gas, which can attain a high reliability under strict conditions, can carry out the real time measurement and the very remote inspection and measurement, and has no risk of occurrence of an accident or the like.

Thus, the present invention provides a method for measuring the methane concentration in a gas, which comprises transmitting light having at least one wavelength band selected from a band of 1.6 $\mu$m and a band of 1.3 $\mu$m through an optical fiber having a small transmission loss in said wavelength bands to a measuring cell where an ambient gas comes in and out, absorbing the light in at least one characteristic absorption wavelength of methane gas, selected from a wavelength of 1.666 $\mu$m and a wavelength of 1.331 $\mu$m, in said measuring cell, transmitting the light through an optical fiber having a small transmission loss in at least one wavelength band selected from a band of 1.6 $\mu$m and a band of 1.3 $\mu$m to a band-pass filter, separating the light into at least one light having the methane gas absorption wavelength, that is, the wavelength to be measured, and at least one light having another reference wavelength, determining the intensity ratio of the light having the wavelength to be measured to the light having the reference wavelength, and calculating the methane gas concentration in the measuring cell from the so-determined intensity ratio.

The present invention further provides an apparatus for measuring the methane concentration in a gas, which comprises a light source emitting light having at least one wavelength band selected from a band of 1.6 $\mu$m and a band of 1.3 $\mu$m, an optical fiber for transmitting said light, which has a small transmission loss in said wavelength bands, a measuring cell where an ambient gas comes in and out, a band-pass filter for separating the light which has been absorbed in at least one characteristic absorption wavelength of methane gas, selected from a band of 1.666 $\mu$m and a band of 1.331 $\mu$m, in the measuring cell into at least one light having the methane gas absorption wavelength and at least one light having other wavelength, a light detector for detecting said lights, and a computer device for processing signals detected by the light detector.

DESCRIPTION OF THE PREFERRED EMBODIMENTS

It was found that an optical fiber recently developed for optical communication, for example, an optical fiber of the quartz type, has a very small transmission loss in the wavelength region of 1.0 to 1.8 $\mu$m, characteristic absorptions of a methane gas are observed in the vicintiy of 1.3 $\mu$m and 1.6 $\mu$m in the above-mentioned wavelength region, and that little substantial absorption of water vapor ($H_2O$) or carbon dioxide ($CO_2$) is present in the vicinity of the characteristic absorption bands at 1.3 $\mu$m and 1.6 $\mu$m. The present invention has been completed based on these findings.

Figure 1:
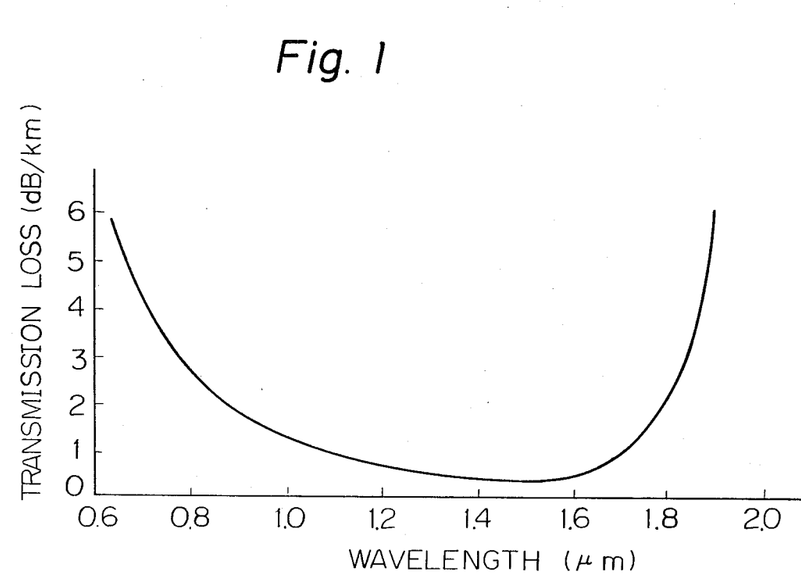
FIG. 1 is a graph showing a transmission loss of an optical fiber of the quartz type to be used in the present invention.

FIG. 1 is a graph showing the transmission loss of an optical fiber of the quartz type in the wavelength region of 0.6 $\mu$m to 1.8 $\mu$m. As is apparent from this graph, the transmission loss is smaller than 1 dB/Km in the wavelength region of 1.1 to 1.7 $\mu$m, and in the vicinity of 1.6

μm, the transmission loss is especially small and about 0.2 dB/Km. It was found that if an optical fiber having such a small transmission loss is used as the optical path, the concentration of a methane gas present in a remote place can be measured according to absorptiometry.

Figure 2:
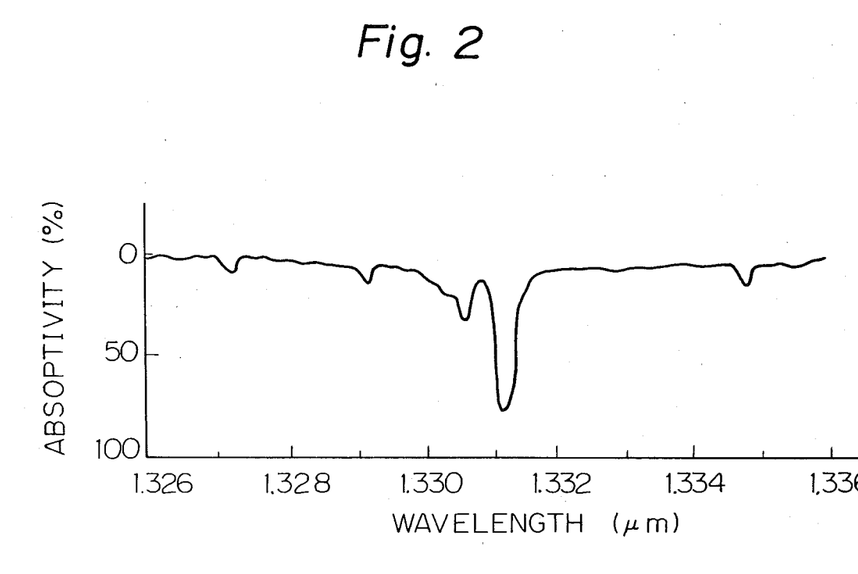
FIG. 2 shows the absorption spectrum of methane gas at a band of 1.33 $\mu$m.
Figure 3:
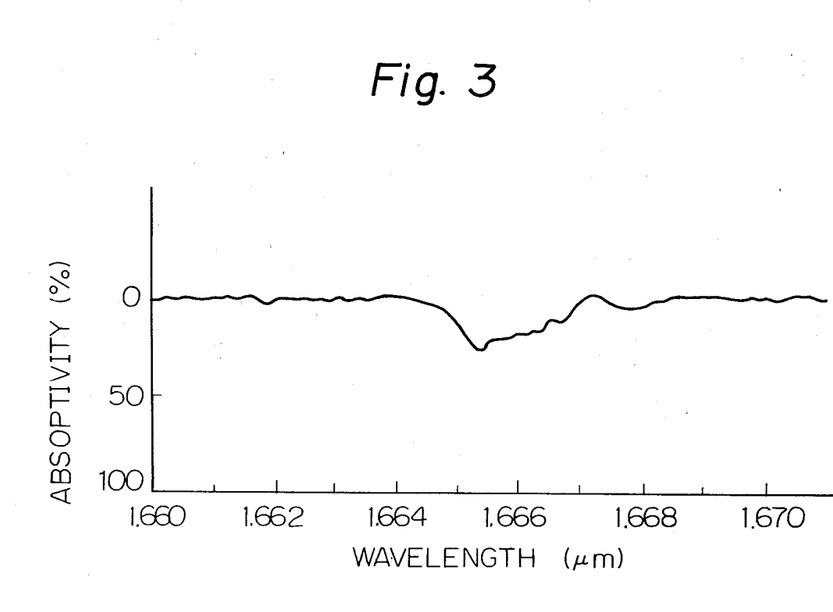
FIG. 3 shows the absorption spectrum of a methane gas at a band of 1.66 $\mu$m.

FIGS. 2 and 3 show the characteristic absorptions of methane gas to be measured according to the present invention, the graph of FIG. 2 shows the characteristic absorption of the methane gas at a band of 1.33 μm, and from FIG. 2, it is seen that a strong absorption band is present at 1.331 μm. The graph of FIG. 3 shows the characteristic absorption of the methane gas at a band of 1.66 μm, and from FIG. 3, it is seen that a relatively strong, broad absorption band is present at 1.66 μm. From the measurement made separately, it was confirmed that no substantial characteristic absorption of $H_2O$ or $CO_2$ is present in the vicinity of these two absorption bands.

However, as pointed out hereinbefore, it was found that characteristic absorption bands of various gases such as hydrocarbon gases other than methane are present in the bands of 1.6 μm and 1.3 μm.

Accordingly, if an optical fiber of, for example, the quartz type is used as a light transmitting path, at least one of the characteristic absorption wavelengths at 1.666 μm and 1.331 μm (the wavelength to be measured) is utilized, the measurement of a methane gas present in a remote place can be performed at a high accuracy without substantial influences of co-present $H_2O$ and $CO_2$. Furthermore, the presence or absence of interference by other hydrocarbon gases can be detected if at least two lights having a wavelength where no substantial absorption of $H_2O$ or $CO_2$ occurs are selected as reference wavelengths, for example, if two wavelengths of 1.30 μm and 1.34 μm are selected as the reference wavelengths when the wavelength of 1.331 μm is chosen as the wavelength to be measured or if wavelengths of 1.30 μm and 1.62 μm are chosen as the reference wavelengths when the wavelengths of 1.331 μm and 1.666 μm are chosen as the wavelengths to be measured, at least two absorption ratios are determined at 1.666 μm or 1.331 μm or at both the wavelengths and the methane concentration measured at 1.666 μm is compared with the methane concentration measured at 1.331 μm, or if at least two reference wavelengths are adopted to obtain a plurality of intensity ratios of the light at the wavelength to be measured to the lights at the reference wavelengths and these intensity ratios are compared with each other.

The light source for emitting near-infrared lights having wavelengths of 1.3 μm and 1.6 μm will now be described. As the light source of this wavelength region, there may be used a gas mantle, a Globar lamp, a Nernst lamp, a tungsten lamp, a xenon lamp and a heated wire, but in view of the handling easiness, durability and power consumption, a semiconductor laser diode (LD) and a light emitting diode (LED) are preferably used.

A high output can be obtained by LD, but the emission wavelength is readily changed according to the temperature and power source voltage and the monochromic characteristic is high. Therefore, a high skill is necessary for using LD in this field. In contrast, although the output of LED is low, the emission spectrum of LED is relatively broad, and therefore, the wavelength stability is good and the characteristic absorption wavelength can be covered very easily. Accordingly, handling of LED is easy and LED can be used satisfactorily according to the kind of a gas to be detected. However, if LED is used as the light source, since the emission spectrum is broad, selection of the wavelength is necessary. Although there are various means for selection of the wavelength, a band-pass filter which is inexpensive is used in the present invention.

The permeation width of the band-pass filter is ordinarily broad in the range of 1 nm to several nm, and if the spectrum line of the object to be measured is narrower than this width, the efficiency is reduced. However, in case of methane gas having a relatively broad width such as 1.331 μm or 1.666 μm, even if the above-mentioned band-pass filter is used, the detection efficiency of the measurement system as a whole can be improved sufficiently. This feature will now be described.

Figure 4:
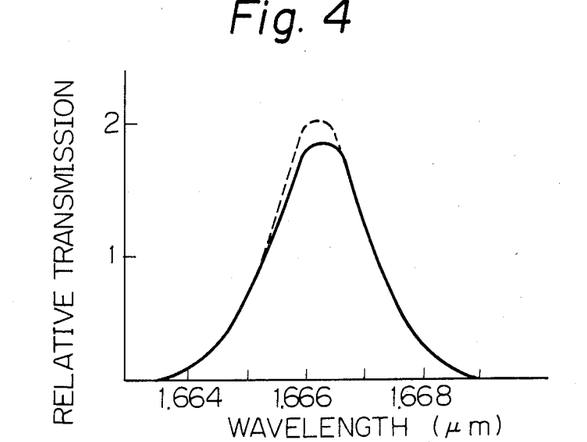
FIG. 4 is a graph showing the intensity distribution of a light which has passed through a band-pass filter of the Gauss distribution type.

FIG. 4 shows the intensity distribution of the light which has passed through a Gauss distribution type band-pass filter having a central wavelength of 1.6661 μm and a half-wave width of 2 nm. The solid line indicates the results obtained when methane gas is contained under a pressure of 20 Torr in a measuring cell having a light path length of 50 cm, and the dot line indicates the results obtained when methane gas is not present. It will be understood that if the difference of the area between both the curves is divided by the area surrounded by the dot line, the absorption ratio of the methane gas can be obtained.

Figure 5:
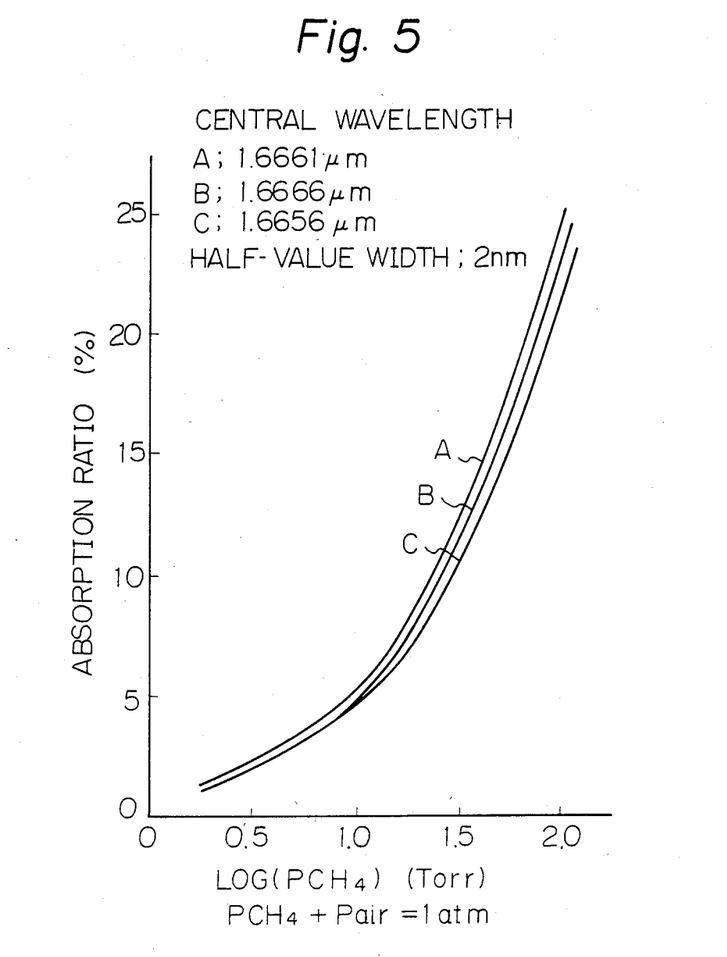
FIG. 5 is a graph showing the relation between the concentration of methane gas and the absorption ratio, which is observed when three kinds of band-pass filters differing in the central wavelength are used.

FIG. 5 is a graph showing the absorption ratio of the absorption spectrum line of methane gas at 1.666 μm, which is obtained by using three kinds of band-pass filters having a half-value width of 2 nm and central wavelengths of 1.6661 μm (A), 1.6666 μm (B) and 1.6656 μm (C), respectively, and changing the methane concentration. The pressure of a mixture of methane and air is 1 atmosphere and the partial pressure (Torr) of the methane gas is changed. As is apparent from the graph, if the central wavelength of the filter is changed, the absorption ratio is changed even when the partial pressure of the methane gas is the same, and the filter (A) having a central wavelength of 1.6661 μm gives a highest absorption ratio.

Figure 6:
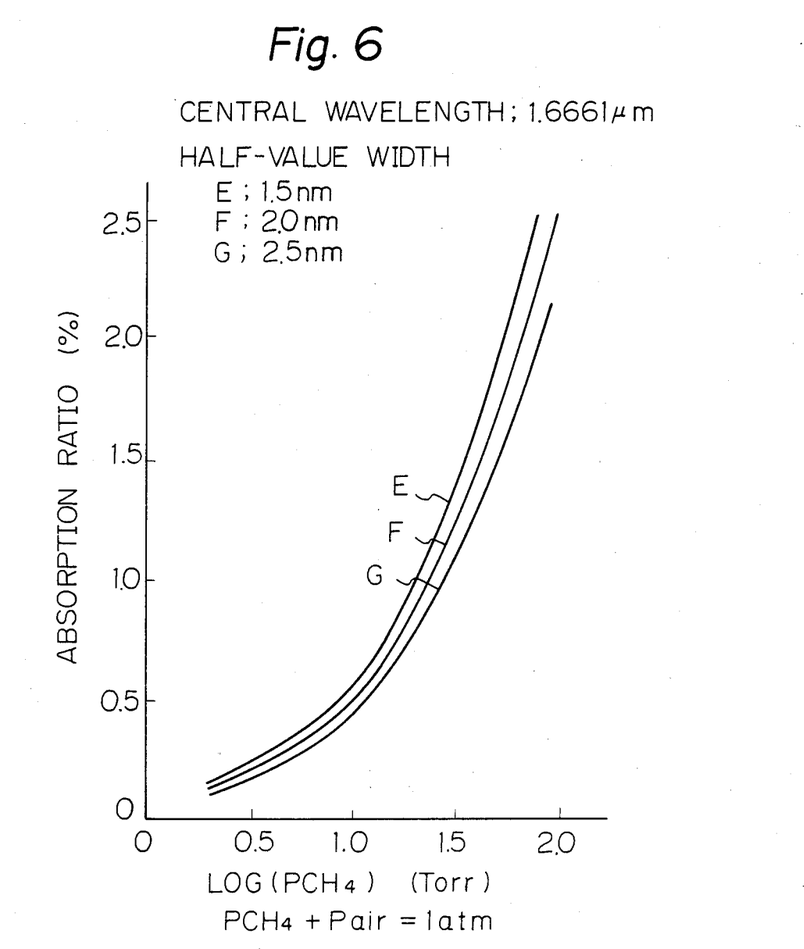
FIG. 6 is a graph showing the relation between the concentration of methane gas and the absorption ratio, which is observed when three kinds of band-pass filters differing in the half-value width.
Figure 7:
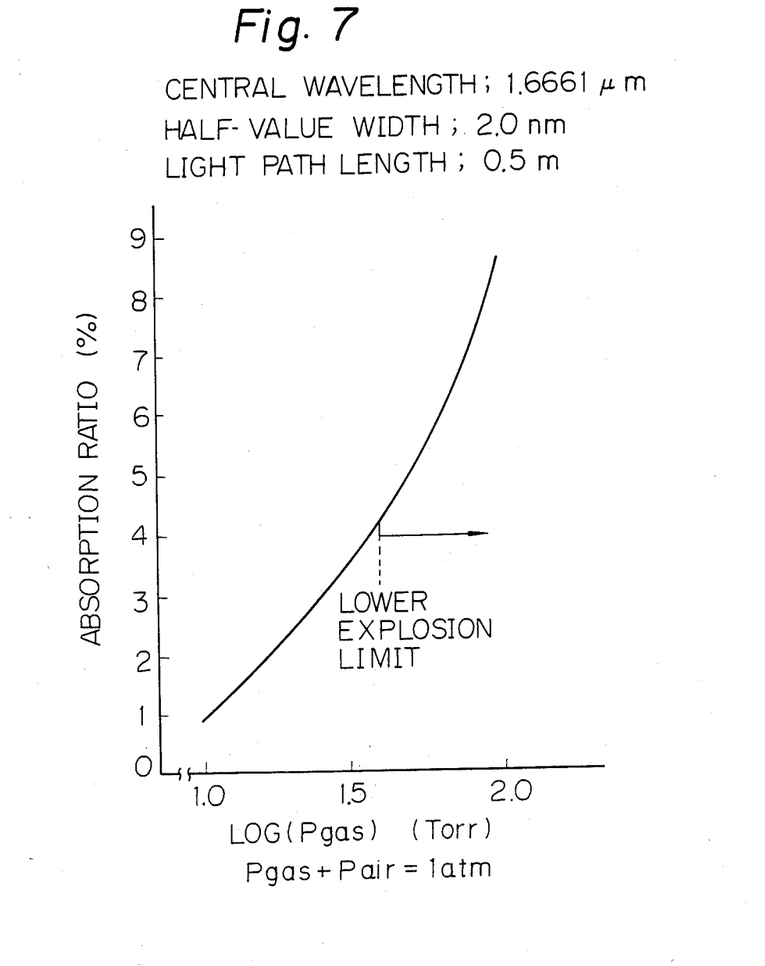
FIG. 7 is a graph showing the relation between the concentration of a city gas in air and the absorption ratio, which is observed at various concentrations of methane gas in air when a band-pass filter is used.

FIG. 6 is a graph showing the absorption ratio of methane gas obtained under the same conditions as in FIG. 5 by using three kinds of band-pass filters having a central wavelength of 1.6661 μm and half-value widths of 1.5 nm (E), 2.0 nm (F) and 2.0 nm (G), respectively. From this graph, it is seen that in order to detect methane gas of 3 Torr in air (corresponding to about 6% of the lower explosion limit concentration), the absorption ratio of about 1.5%, that is, the light intensity reduction of about 1.5%, should be measured by using the filter (G) having a half-value width of 2.5 nm. Incidentally, although it is seen from FIG. 6 that the filter (E) gives a highest sensitivity, the filter having a narrow half-value width is relatively expensive, and since it is found that the filter (G) can be used satisfactorily, the filter (G) is selected. Similar examinations have been made on a city gas containing methane gas. FIG. 7 is a graph showing the absorption ratio measured by using a sample composed of a mixture of air with a city gas containing 20% of methane and changing the amount of the city gas in the mixture. The band-pass filter used has a central wavelength of 1.6661 μm and a half-value width of 2.0 nm.

From the foregoing experimental results, it is seen that even if a small type LED is used as the light source and a band-pass filter is used for selection of the wavelength, the methane gas concentration can be determined quantitatively. Furthermore, if the methane gas concentration is determined from the absorption ratios of at least one measurement wavelength selected from characteristic absorption wavelengths of methane gas at 1.666 $\mu$m and 1.331 $\mu$m to a plurality of reference wavelengths, interference by hydrocarbon gases other than methane can be detected. Although a certain hydrocarbon gas other than methane has characteristic absorption bands of 1.6 $\mu$m and 1.3 $\mu$m, since the molecular absorptivity at 1.666 $\mu$m is different from the molecular absorptivity at 1.331 $\mu$m and since the molecular absorptivity of the hydrocarbon gas is different from those of the methane gas when a plurality of reference wavelengths close to the wavelength to be measured are adopted, if a hydrocarbon gas other than the methane gas is present, the methane concentration measured at 1.666 $\mu$m is not in agreement with the methane concentration measured at 1.331 $\mu$m, or the absorption ratios of one measurement wavelength to the reference wavelengths are different from each other and the methane concentrations are not in agreement with each other, and by this disagreement, interference by a hydrocarbon gas other than methane can be confirmed.

Figure 8:
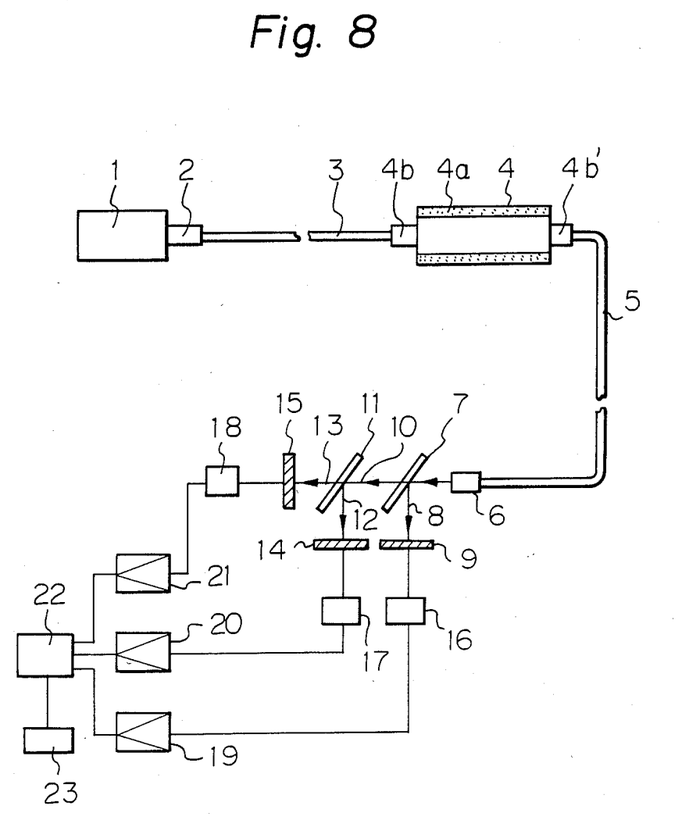
FIGS. 8 and 9 are diagrams showing embodiments of the methane gas concentration measuring apparatus according to the present invention; and, FIGS. 10 and 11 are diagrams showing other embodiments of the methane gas concentration measuring apparatus according to the present invention.

FIG. 8 shows an example of the methane gas concentration measuring apparatus constructed based on the foregoing findings. In FIG. 8, reference numeral 1 indicates a light source comprising a light emitting diode (LED). A light emitted from this light source 1, which has at least one wavelength band selected from a band of 1.3 $\mu$m and a band of 1.6 $\mu$m, is transmitted to a light transmission path 3 composed of an optical fiber having a small transmission loss, such as an optical fiber of the quartz type, through an optical coupler 2. The optical fiber 3 of the quartz type has transmission characteristics as shown in FIG. 1 and has a very small transmission loss in the wavelength region of 1.1 to 1.7 $\mu$m. Accordingly, the length of the optical fiber may be increased to several to about 10 Km. The light from the optical fiber 3 of the quartz type is transmitted to a measuring cell 4 through an optical coupler 4b. The measuring cell 4 comprises a circular cylinder 4a and optical couplers 4b and 4b' mounted on both the ends of the cylinder 4a, and the cylinder 4a is composed of a porous sintered metal or a plastic foam having a continuous cell structure so that a gas to be measured is allowed to freely come in the measuring cell 4 and come out therefrom. While the light is transmitted from the optical coupler 4a to the optical coupler 4b' in the cell, a light having a specific wavelength is absorbed. The optical path length (the distance between the optical couplers 4b and 4b') of the measuring cell 4 is not particularly critical, but in many cases, it is adjusted to 50 to 100 cm. When the concentration of the methane gas is low, a known multiple path type absorption cell may be used. The light from the measuring cell 4 is transmitted to an optical fiber having a small transmission loss, for example, an otpical fiber 5 of the quartz type, through the optical coupler 4b'. Also this optical fiber 5 of the quartz type is characterized by a small transmission loss. The light which has passed through the optical fiber 5 is transmitted to a beam splitter 7 comprising a half-mirror from an optical coupler 6, and the light is divided into two light fluxes in the beam splitter 7. The first light flux 8 is transmitted to a first band-pass filter 9 and the second light flux 10 is transmitted to a second beam splitter 11 and is further divided into a third light flux 12 and a fourth light flux 13. The third light flux 12 is transmitted to a second band-pass filter 14 and the fourth light flux 13 is transmitted to a third band-pass filter 15.

Each of the filters 9, 14 and 15 is an interference filter in which the light-interfering action of a thin film is utilized, and a multi-layer film interference filter is preferably used and it is preferred that the percent transmission at the central wavelength be as high as possible and the half-value width be as narrow as 1.0 to 2.0 nm. The central wavelength of the first filter 9 is adjusted to 1.3312 $\mu$m and the central wavelength of the second filter 14 is adjusted to 1.30 $\mu$m, which is not a characteristic absorption wavelength of methane and has no substantial characteristic absorption of $H_2O$ or $CO_2$.

Also the third filter 15 is for the reference wavelenth and its central wavelength is adjusted to 1.34 $\mu$m. The light which has passed through the first filter 9 is a light of the Gauss type transmitted wavelength distribution having the intensity reduced by the absorption due to the methane gas, and the lights which have passed through the second and third filters 14 and 15 are irrelevant to the absorption by the methane gas and each of these lights has a central wavelength in the vicinity of the methane absorption wavelength of 1.331 $\mu$m and has a Gauss type wavelength distribution. These lights are transmitted to first, second and third light detectors 16, 17 and 18, each of which comprises an avalanche photodiode (APD) or a photodiode (PD) (for example, a Ge semiconductor), and they are converted to electric signals, amplified by amplifiers 19, 20 and 21 and supplied to a signal processing device 22 comprising a microcomputer.

In the signal processing device 22, the electric signal detected by the first light detector 16 is compared with the electric signal detected by the second light detector 17, and the extinction ratio A of methane is determined from the intensity ratio of the light at a wavelength of 1.3312 $\mu$m to the light at a wavelength of 1.30 $\mu$m and the computing processing is carried out by utilizing the relation between the extinction ratio A and the methane gas concentration, which has been determined in advance by using a standard methane gas, whereby the concentration of the methane gas in the gas present in the measuring cell 4 is determined at 1.3312 $\mu$m. Simultaneously, the electric signal detected by the first light detector 16 is compared with the electric signal detected by the third light detector 18 and the absoprtion ratio A' of methane is determined from the intensity ratio of the light at a wavelength of 1.3312 $\mu$m to the light at a wavelength of 1.34 $\mu$m, and the methane concentration is determined in the same manner as described above. The so-determined two concentrations are compared with each other, and if both the concentrations are identical within an allowable error range, the result is indicated as a methane gas concentration in the gas in the measuring cell 4 on a display 23. When a difference exceeding a predetermined value is present between the two measured concentrations, it means that a hydrocarbon gas other than methane is contained in the gas in the measuring cell 4 or an accident or trouble is caused in the portion downstream of the optical coupler 6 in the measuring apparatus, that is, in the beam splitter 7 or 11, the band-pass filter 9, 14 or 15, the light detector 16, 17 or 18 or the amplifier 19, 20 or 21. This is indicated on the display 23. Incidentally, if a testing light source is disposed between the light coupler 6 and the first beam splitter 7, and if the light from the light coupler 6 is cut and the testing light source is actuated when a trouble is observed, occurrence of an accident in the measuring apparatus is detected or the inhibition by a hydrocarbon gas other than methane is confirmed.

Figure 9:
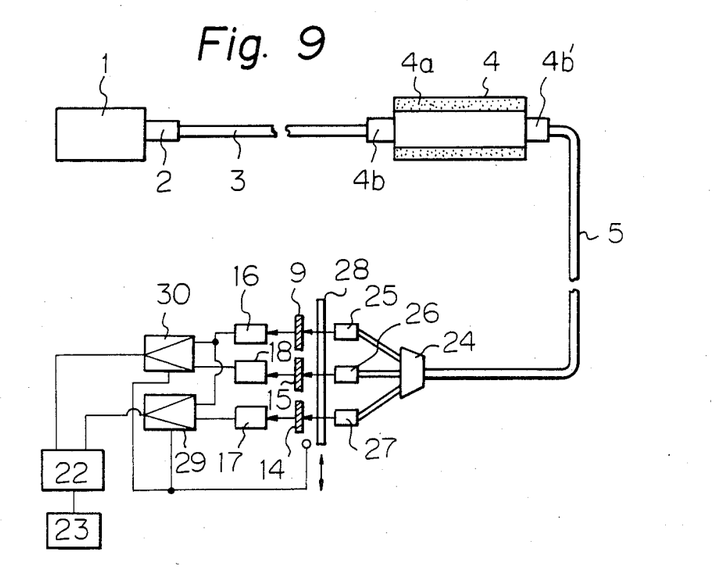

FIG. 9 illustrates another embodiment of the measuring apparatus of the present invention. The same structural members as in FIG. 8 are represented by the same reference numerals, and explanations of these members are omitted. In this embodiment, a light from the measuring cell 4 is passed through an optical fiber 5 having a small transmission loss, such as an optical fiber of the quartz type, and is divided into three light fluxes by a light branching path 24. The present embodiment is different from the embodiment shown in FIG. 8 in the point where these light fluxes are passed through a chopper 28 from light couplers 25, 26 and 27 and transmitted to first, second and third filters 9, 14 and 15, respectively, and the electric signals from the first and second light detectors 16 and 17 are transmitted to an amplifier 29 and the electric signals from the first and third light detectors 16 and 18 are transmitted to an amplifier 30. In the present embodiment, the electric signals from the light detectors 16, 17 and 18 are converted to alternating curent signals by the chopper 28, and therefore, the present embodiment is advantageous in that amplification can be accomplished with ease.

The present invention is not limited to the foregoing embodiments. For example, there may be adopted a modification in which a light from the light source is divided into a plurality of lights by a light branching path and these lights are transmitted to a plurality of measuring cells 4 through independent optical fibers 3 of the quartz type so that methane concentrations at different points can simultaneously be measured.

Figure 10:
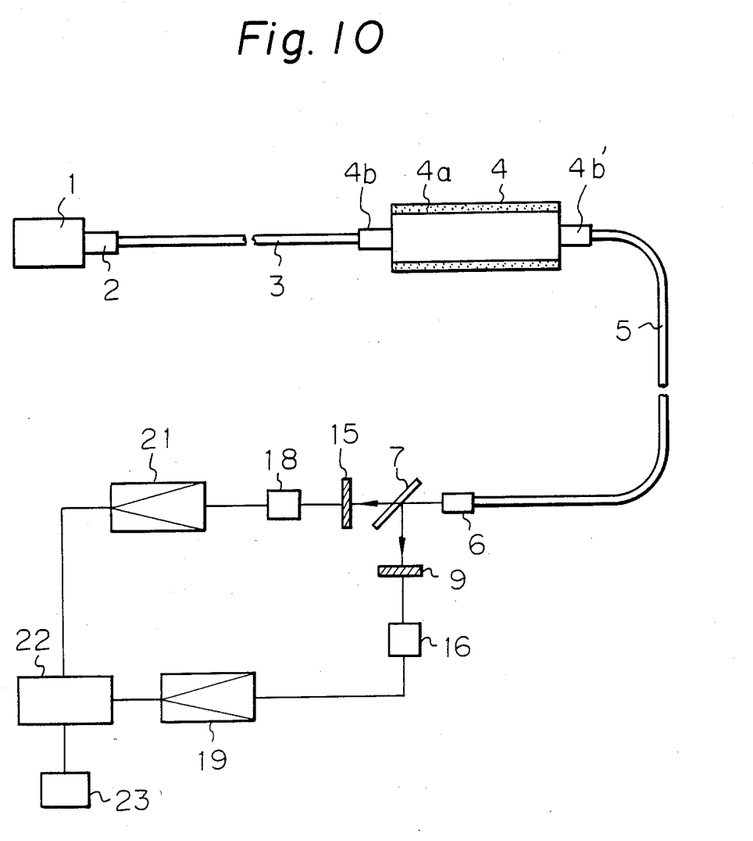
Figure 11:
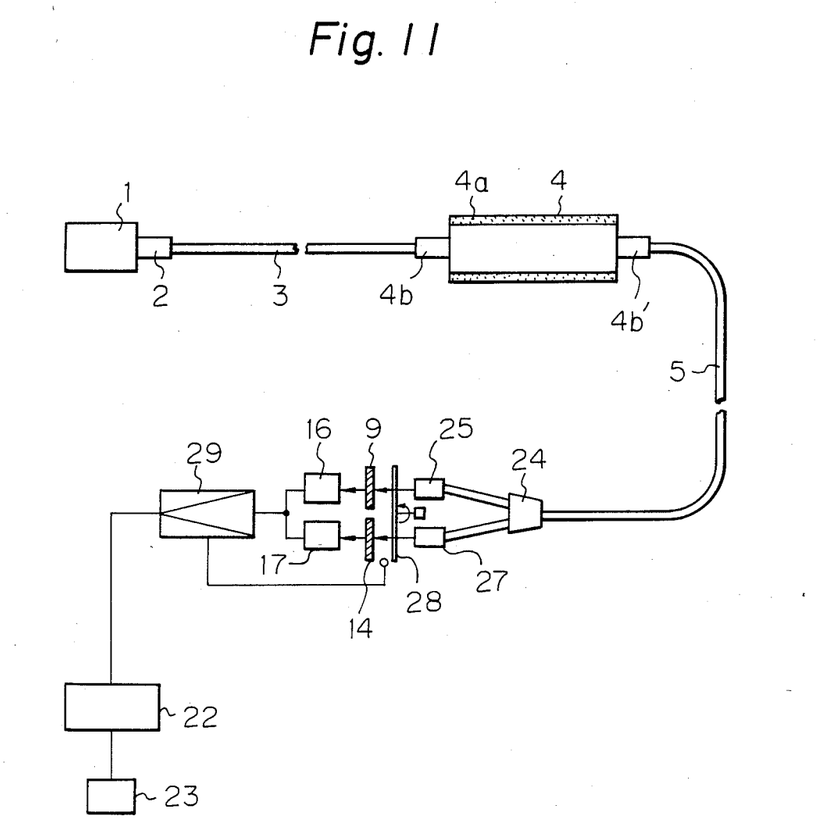

FIGS. 10 and 11 illustrate further embodiments of the measuring apparatus of the present invention, in which the same structural members as in FIGS. 8 and 9 are represented by the same reference numerals. The apparatus illustrated in FIG. 10 has basically the same structure as that in FIG. 8 except that the light is only once divided into two light fluxes in the beam splitter 7, which are then transmitted to a first band-pass filter 9 and to a second band-pass filter 15. The apparatus illustrated in FIG. 11 has basically the same structure as that in FIG. 9 except that the light is divided into only two light fluxes by a light branching path 24.

As is apparent from the foregoing description, according to the methane gas concentration measuring method and apparatus of the present invention, at least one absorption band selected from bands of 1.33 $\mu$m and 1.66 $\mu$m where the transmission loss of the optical fiber is smallest and no substantial absorption of $CO_2$ or $H_2O$ is caused is adopted as the characteristic absorption band for the methane gas, an optical fiber having a small transmission loss is used as the light transmitting path, a band-pass filter which has a small size and is inexpensive is used for selection of the wavelength, and the absorption ratio of at least one wavelength selected from 1.33 $\mu$m and 1.66 $\mu$m to at least one reference wavelength is used to effect the determination of the methane concentration. Accordingly, a measuring cell 4 can be located in a very remote place, and an influence of electromagnetic induction is eliminated and occurrence of an accident such as formation of a short circuit due to breakage of a cable can be prevented. Therefore, the method and apparatus of the present invention are suitably applied to the measurement of the methane gas concentration in a gallery gas in a coal mine or to the concentrated inspection of the methane gas concentration at one point by arranging a plurality of measuring cells in a broad region of an underground shopping mall or the like. Furthermore, since the measurement is not substantially influenced by $H_2O$ or $CO_2$ present in the gas to be measured, the measurement accuracy can be increased. Since at least one wavelength selected from 1.331 $\mu$m and 1.666 $\mu$m is adopted as the measurement wavelength and one or more reference wavelengths are used for determination of the methane gas concentration, by comparing the measured values with each other, it can be confirmed whether or not a hydrocarbon gas other than methane is present in the gas to be measured, and occurrence of an accident in the measuring apparatus can be detected and the reliability of the obtained results can be increased. Moreover, since the absorptiometry is adopted, the real time measurement is possible and a change of the methane concentration can be promptly coped with. Still further, since a band-pass filter is used for selection of the wavelength, the size and manufacturing cost of the apparatus can be reduced, and even if a light transmitting diode having a small size and a small output with a small power consumption, for which cooling is not necessary, is employed, a methane concentration lower than the explosion limit of methane can be detected with a high sensitivity.

I claim:

1. A method for measuring the methane concentration in a gas, which comprises:

transmitting light having at least one wavelength band selected from a band of 1.6 $\mu$m and a band of 1.3 $\mu$m through an optical fiber having a small transmission loss in said wavelength bands to a measuring cell where a gas whose methane concentration is to be measured passes in and out, absorbing the light in at least one characteristic absorption wavelength of methane gas, selected from a wavelength of 1.666 $\mu$m and a wavelength of 1.331 $\mu$m, in said measuring cell, transmitting light passing through the measuring cell through an optical fiber having a small transmission loss in at least one wavelength band selected from a band of 1.6 $\mu$m and a band of 1.3 $\mu$m to a band-pass filter, separating the light into at least one light having the methane gas absorption wavelength, to be measured, and at least two lights having other reference wavelengths, determining the intensity ratio of the light having the wavelength to be measured to the lights having the reference wavelengths, and calculating the methane gas concentration in the measuring cell from the so-determined intensity ratio.

2. A method as claimed in claim 1 wherein the optical fiber is an optical fiber of the quartz type.

3. A method as claimed in claim 1, wherein the gas whose methane concentration is to be measured additionally contains $H_2O$ and/or $CO_2$ and wherein said methane gas concentration is determined without adverse influences due to the $H_2O$ and/or $CO_2$ co-present.

4. A method as claimed in claim 3, wherein two wavelengths of 1.30 $\mu$m and 1.34 $\mu$m are selected as the reference wavelength when the wavelength of 1.331 $\mu$m is chosen as the wavelength of methane gas to be measured.

5. A method as claimed in claim 3, wherein two wavelengths of 1.30 $\mu$m and 1.62 $\mu$m are selected as the reference wavelength when the wavelengths of 1.331

μm and 1.666 μm are chosen as the wavelength of methane gas to be measured.

6. A method as claimed in claim 1, wherein said gas whose methane concentration is to be measured contains a hydrocarbon gas other than methane and wherein said method includes detecting interference by said other hydrocarbon gas.

7. A method as claimed in claim 6, wherein the methane concentration is determined from the absorption ratio of at least one measurement wavelength selected from characteristic absoption wavelengths of methane gas at 1.666 μm and 1.331 μm to a plurality of reference wavelengths.

8. An apparatus for measuring the methane concentration in a gas, which comprises:
   a light source emitting light having at least one wavelength band selected from a band of 1.6 μm and a band of 1.3 μm,
   an optical fiber for transmitting said light, which has a small transmission loss in said wavelength bands,
   a measuring cell where a gas whose methane gas concentration is to be measured passes in and out,
   a band-pass filter for separating the light which has been absorbed in at least one characteristic absorption wavelength of a methane gas, selected from a wavelength of 1.666 μm and a wavelength of 1.331 μm, in the measuring cell into which at least one light having the methane gas absorption wavelength and at least two lights having other wavelengths are passed,
   a light detector for detecting said lights, and
   a computer for processing signals detected by the light detector.

9. An apparatus as claimed in claim 8, wherein the optical fiber consists of an optical fiber of the quartz type.

10. An apparatus as claimed in claim 9, wherein the light source is selected from the group consisting of a gas mantle, a Globar lamp, a Nernst lamp, a tungsten lamp, a xenon lamp, a heated wire, a semiconductor laser diode and a light emitting diode.

11. An apparatus as claimed in claim 10, wherein the light source is selected from the group consisting of a semiconductor laser diode and a light emitting diode.

12. An apparatus as claimed in claim 9, wherein the band-pass filter has a central wavelength of 1.6661 μm and a half-value width of 1.5, 2.0 or 2.5 nm.

13. An apparatus as claimed in claim 9, wherein the measuring cell comprises a circular cylinder made of a porous sintered metal or made of a continuous cell structure plastic foam and optical couplers mounted on both ends of the circular cylinder.

14. An apparatus as claimed in claim 9, wherein the measuring cell consists of a multiple path type absorption cell.

* * * * *